US008128648B2

(12) United States Patent
Hassidov et al.

(10) Patent No.: US 8,128,648 B2
(45) Date of Patent: Mar. 6, 2012

(54) CHEST DRAINAGE AND APPARATUS FOR THE INSERTION THEREOF

(75) Inventors: Noam Hassidov, Bostan Hagalil (IL); Merav Somer-Lapid, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 198 days.

(21) Appl. No.: 12/450,725

(22) PCT Filed: Apr. 14, 2008

(86) PCT No.: PCT/IB2008/000898
§ 371 (c)(1),
(2), (4) Date: Dec. 18, 2009

(87) PCT Pub. No.: WO2008/125961
PCT Pub. Date: Oct. 23, 2008

(65) Prior Publication Data
US 2010/0100032 A1   Apr. 22, 2010

Related U.S. Application Data

(60) Provisional application No. 60/907,696, filed on Apr. 13, 2007.

(51) Int. Cl.
*A61B 17/34* (2006.01)
(52) U.S. Cl. .................. 606/185; 604/164.01
(58) Field of Classification Search .............. 606/167, 606/174, 180, 184, 185; 60/164.01–164.06, 60/264
See application file for complete search history.

(56) References Cited

U.S. PATENT DOCUMENTS

| 5,817,062 A * | 10/1998 | Flom et al. ........... 604/164.04 |
| 5,971,960 A * | 10/1999 | Flom et al. ........... 604/174 |
| 6,030,402 A * | 2/2000 | Thompson et al. ....... 606/185 |
| 6,402,770 B1 | 6/2002 | Jessen |
| 2002/0099402 A1 | 7/2002 | Buckman et al. |
| 2003/0208153 A1 | 11/2003 | Stenzel |
| 2003/0225402 A1 | 12/2003 | Stevens et al. |
| 2005/0234390 A1 | 10/2005 | Buckman et al. |
| 2006/0174898 A1 | 8/2006 | Brown |

FOREIGN PATENT DOCUMENTS

DE    100 37 421 A1    5/2002

OTHER PUBLICATIONS

The International Search Report for PCT/IB2008/000898; 3 pages; mailed Nov. 27, 2008.

* cited by examiner

*Primary Examiner* — Kevin T Truong
(74) *Attorney, Agent, or Firm* — The Nath Law Group; Susanne M. Hopkins; William L. Kilma

(57) ABSTRACT

An apparatus for the introduction of a drainage tube into a patient's chest cavity, comprising a housing having a distal end, a proximal end, and a longitudinal axis; a scalpel operable in a protruding position between a closed position in which the cutting portions are adjacent one another and adapted to make an incision in the dermis of the patient, and an open position in which the cutting portions are spaced from one another forming a scalpel passage along the longitudinal axis between the cutting portions. The apparatus further comprising a trocar comprising first and second trocar portions, each extending along the length of the trocar; the trocar being operable between an closed position wherein the first and second trocar portions are substantially adjacent one another, and a closed position in which the first and second trocar portions are spaced from one another and adapted for the introduction of the drainage tube therethrough.

20 Claims, 11 Drawing Sheets

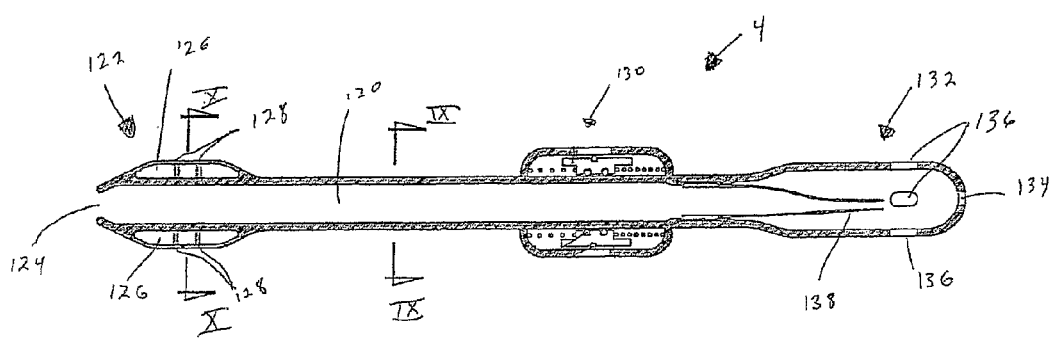
FIG 8
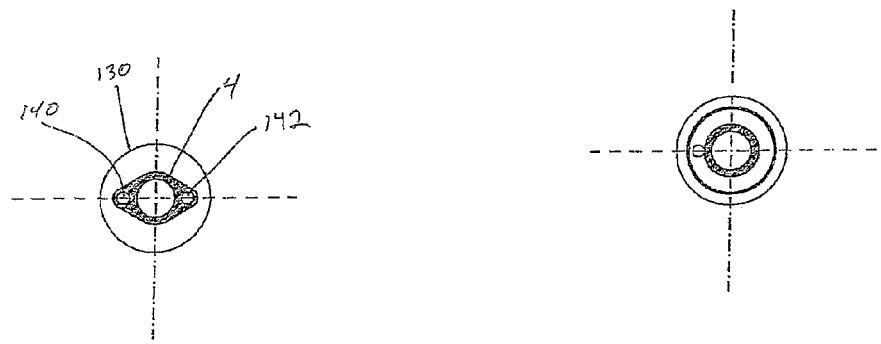
FIG 9
FIG 10

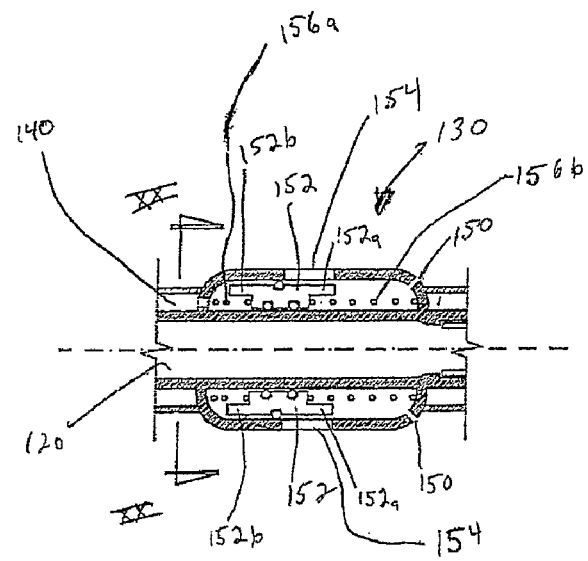
Fig. 18
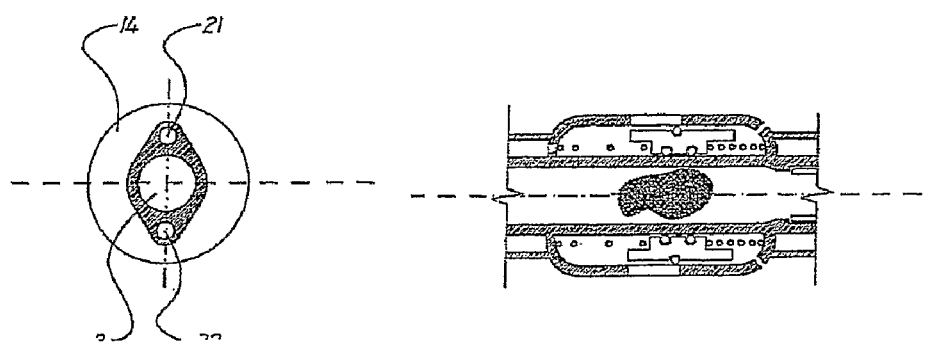
Fig. 20
Fig. 19

CHEST DRAINAGE AND APPARATUS FOR THE INSERTION THEREOF

This is a National Phase Application filed under 35 U.S.C. 371 as a national stage of PCT/IB2008/000898, filed Apr. 14, 2008, an application claiming the benefit under 35 U.S.C. 119(e) U.S. Provisional Application No. 60/907,696, filed Apr. 13, 2007, the content of each of which is hereby incorporated by reference in its entirety.

FIELD OF THE INVENTION

This invention relates to devices for the drainage of fluid from a patient's body, and, particularly, for the drainage of air from pleural space in a patient's chest cavity. In addition, it relates to apparatuses adapted to insert such devices into the chest cavity.

BACKGROUND OF THE INVENTION

Chest drainage tubes for the drainage of air trapped in a patient's thorax or pleural space (hereafter referred to collectively as a "chest cavity") are often used to allow for drainage of air trapped therein following trauma. Typically, such chest tubes have one or more holes at a distal end, and a lumen in fluid communication therewith via which the air is evacuated from the patient's body. The chest tubes typically include features, e.g., shutoff valves and/or duckbill valves, to prevent backflow of air into the chest cavity.

Chest tubes are typically inserted into a patient's chest cavity with a trocar mounted to the internal lumen. The trocar is stiff, substantially pointed at the distal end, and allows for advancement of the flexible chest drainage tube into an incision in the chest wall. Such a trocar is useful for initial insertion of the chest tube, but becomes a dangerous instrument once the chest tube is advanced below the level of the ribs.

One consideration when inserting a drainage tube into a patient's chest cavity is maintaining sterility of the site. Inserting of the chest tube, especially in an emergency setting, requires a sterile scrubbing of the incision area and incision into the chest wall with sterile instruments. These incisions are, understandably, difficult to perform aseptically in the field, where the insertion site may be bloody, dirty, or otherwise contaminated. In addition, maintenance of sterility in the area of chest tube penetration into the chest has been difficult as has been the ability to hold the chest tube in position once it has been introduced into the patient. The use of surgical gloves to maintain sterility becomes problematic since the gloves become contaminated quickly in the typical field environment.

US 2005/0234390 discloses a device which utilizes a chest tube with a cutting distal end and a central blunt trocar. The blunt trocar or obturator shields the sharp cutting distal end of the chest tube until controllably retracted. Once the blunt trocar or obturator is retracted, the chest tube is advanced out through its sterile, protective package and into the patient. The blunt trocar is advanced back into its position to shield the sharp tip of the chest tube during patient insertion. The chest tube also includes a hold-down mechanism that is created by an adhesive seal to the patient's chest and ribbons or straps that are wrapped around the chest tube once it is correctly positioned. The straps include adhesive ends to grip the chest tube once the straps are in place.

SUMMARY OF THE INVENTION

According to one aspect of the present invention, there is provided an apparatus for the introduction of a drainage tube into a patient's chest cavity, the apparatus comprising:

- a housing having a distal end, a proximal end, and a longitudinal axis;
- a scalpel mechanism comprising two cutting portions at a distal end thereof and being mounted inside the housing, the scalpel mechanism being adapted to penetrate the distal end of the housing toward a protruding position therefrom, and being operable in the protruding position between a closed position in which the cutting portions are adjacent one another and adapted to make an incision in the dermis of the patient, and an open position in which the cutting portions are spaced from one another forming a scalpel passage along the longitudinal axis between the cutting portions; and
- a trocar (i.e., a sharp-pointed surgical instrument, used with a cannula to puncture a body cavity for fluid aspiration) with a proximal end and a distal end and comprising first and second trocar portions, each extending along the length of the trocar and being separable from one another; the trocar being operable between an closed position wherein the first and second trocar portions are substantially adjacent one another, and a closed position in which the first and second trocar portions are spaced from one another and adapted for the introduction of the drainage tube therethrough.

The distal end of the housing may be formed as a rounded tip (i.e., the cross-section of the distal end taken through a plane containing the longitudinal axis is substantially arcuate). This allows the distal end of the housing to "find" the space between the ribs when pressed against the chest of a patient.

The apparatus may comprise means for securing the drainage tube within the chest cavity when inserted therein. When the drainage tube is secured within the chest cavity, at least the housing, scalpel mechanism, and trocar may be adapted to be removed therefrom.

The trocar may comprise at its proximal end a stopping mechanism adapted to prevent the trocar from progressing distally within the chest cavity beyond a predetermined amount. According to this embodiment, the trocar may comprise a trocar head being operable in a compressed position and an expanded position in which it protrudes radially from the rest of the trocar, and comprise expansion means adapted to spontaneously bring the trocar head into its expanded position; the stopping mechanism being adapted to be activated upon expansion of the trocar head.

The trocar may further comprise a trocar head adjacent the distal end of the trocar, the trocar head being operable in a compressed position in which it is substantially flush with the rest of the trocar, and an expanded position, in which it protrudes radially therefrom. The housing may be adapted to enclose the trocar so as to retain the trocar in its closed position with the trocar head in its compressed position.

The trocar head may be adapted to remain in its expanded position in the absence of any net external force thereto, and to assume its compressed position in the presence of an inwardly directed radial force.

The trocar head may comprise adjacent or at its distal end two or more hinged arms, each comprising two arm segments hingedly articulated to its adjacent segment or the trocar, each arranged such in the compressed and expanded positions of the trocar head, distal and proximal ends thereof remain equal distances from the longitudinal axis.

The apparatus may constitute a part of a device for chest drainage with the tube constituting a part of the device and being mounted in the housing before the introduction of the drainage tube into the patient's chest cavity.

The tube may comprise a proximal end and a distal end and being adapted to pass through the trocar passage until its distal end protrudes therefrom along the longitudinal axis, to a predetermined extent necessary for the insertion into the chest.

The tube may be fitted at its distal end with an inflatable balloon portion to secure it within the chest cavity when inserted therein. The balloon portion may be formed with drainage channels which provide fluid communication between the exterior of the balloon portion with the interior of the tube.

The tube may comprise a one-way valve at its proximal end.

The tube may be fitted with a stopper adapted to prevent movement thereof in the distal direction when the housing when the scalpel mechanism and the trocar are removed from the tube.

The tube may be fitted with an indicating unit, including a pressure indicator and a channel extending from the distal end of the tube, and open to the exterior thereof, to the pressure indicator.

According to another aspect of the present invention, there is provided a drainage tube for introduction of a drainage tube into a patient's chest cavity, the drainage tube having a proximal end and a distal end and comprising means at the distal end for being secured therein.

The tube may be fitted at its distal end with an inflatable balloon portion to provide the securing.

The balloon portion may comprise drainage channels which provide fluid communication between the exterior of the balloon portion and the interior of the tube.

The tube may further comprise one or more of the followings:

a one-way valve at its proximal end;

a stopper adapted to prevent movement thereof in the distal direction; and/or an indicating unit adapted to provide an indication of a blockage within the tube.

According to a further aspect of the present invention, there is provided a method of insertion of a drainage tube into a patient's chest cavity, including:

providing an apparatus according as described above;

pressing the distal end of the base against the patient's chest, until the drainage tube is within the chest cavity;

inflating a balloon portion, provided at a distal end of the drainage tube; and removing the apparatus from the patient, leaving the drainage tube.

The method may further include the step of providing a stopper on the drainage tube adjacent the patient's chest.

Hereafter in the specification and claims, the term "distal" will be used to indicate portions of the apparatus and/or its constituent elements which, during use, are adapted to be closer to the patient, and the term "proximal" will be used to indicate portions of the apparatus and/or its constituent elements which, during use, are adapted to be farther from the patient.

BRIEF DESCRIPTION OF THE DRAWINGS

In order to understand the invention and to see how it may be carried out in practice, embodiments will now be described, by way of non-limiting examples only, with reference to the accompanying drawings, in which:

FIG. 8 is a longitudinal cross-sectional view of a tube used in the apparatus shown in FIG. 1, with a balloon at its distal end deflated;

FIGS. 9 and 10 are cross-sectional views of the tube shown in FIG. 8, taken along lines IX-IX and X-X, respectively;

FIGS. 18 and 19 are longitudinal cross-sectional views of a portion of the tube shown in FIG. 8 and taken in a plane substantially perpendicular to that of FIG. 8, including a pressure indicator, with a clear drainage pipe and an obstructed drainage pipe, respectively;

FIG. 20 is a cross-sectional view of the portion of the tube shown in FIG. 18, taken along a line XX-XX;

DETAILED DESCRIPTION OF EMBODIMENTS

Figure 1:
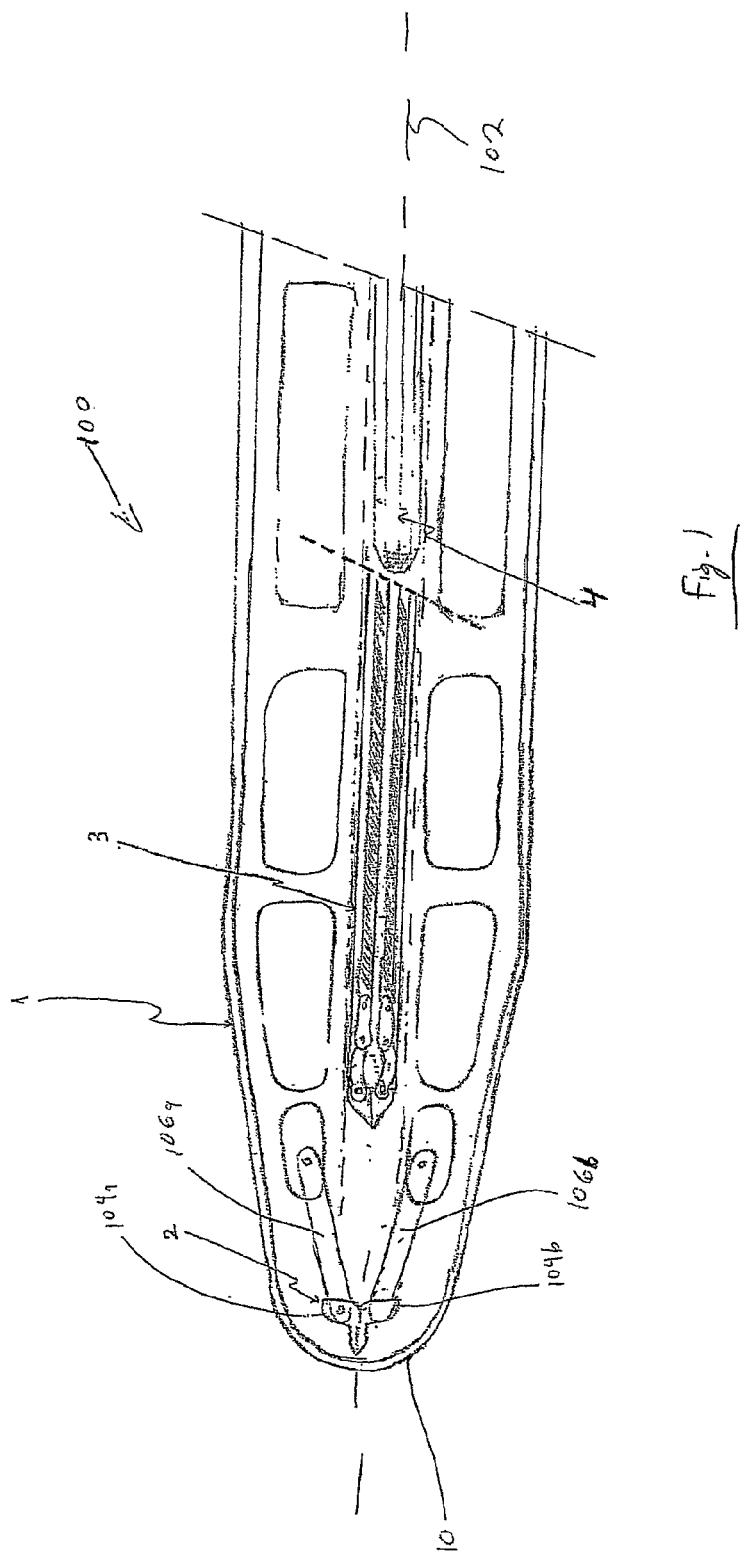
FIG. 1 is a partial schematic view of the interior of an apparatus according to one embodiment of the present invention.

As illustrated in FIG. 1, there is provided an apparatus, which is generally indicated at 100, for the introduction of a drainage tube into a patient's chest cavity. The apparatus 100 comprises a housing 1, a scalpel mechanism 2, a trocar 3, and a drainage tube 4. The elements of the apparatus 100 are arranged such that initially, the scalpel mechanism 2 is located distally of the trocar 3, and the trocar is located distally of the drainage tube 4.

The housing 1 is formed as an elongate pipe made of hard material, such as injected plastic, and has a longitudinal axis 102 along the center thereof. A distal end 10 of the housing is rounded in three-dimensions.

Figure 2:
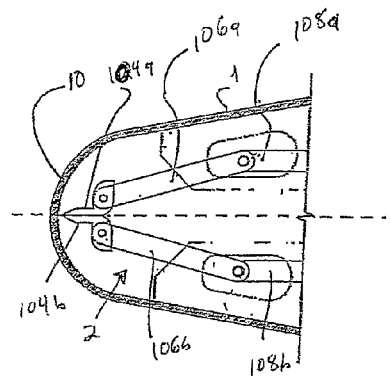
FIGS. 2, 3, and 4 are schematic views of a scalpel mechanism of the apparatus shown in FIG. 1, at different stages of their operation.
Figure 3:
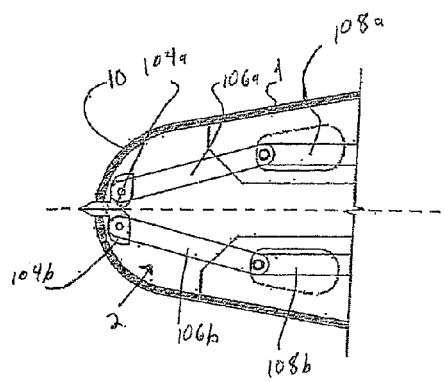
Figure 4:
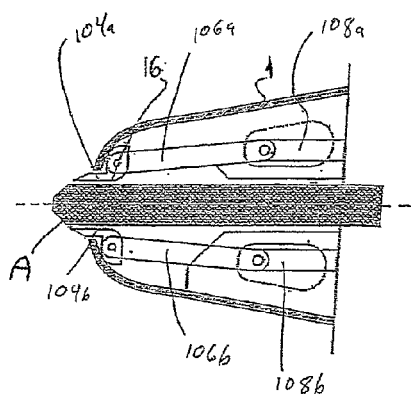

As best seen in FIGS. 2 through 4, the scalpel mechanism 2 comprises two cutting portions 104a, 104b, which are arranged opposite one another. FIG. 1 illustrates scalpel mechanism 2 in its closed position, wherein the cutting portions 104a, 104b are adjacent one another. The scalpel mechanism further comprises scalpel supports 106a, 106b, each being hingedly articulated to one of the cutting portions 104a, 104b at its distal end, and hingedly mounted within the housing at its proximal end, for example to positioning chokes 108a, 108b.

The scalpel mechanism 2 is adapted to be moved distally along the longitudinal axis 102, and pierce the distal end 10 of the housing 1 to be brought into a protruding position wherein the cutting portions 104a, 104b project from the distal end of the housing, while remaining in its closed position. In this protruding position, the cutting portions 104a, 104b project sufficiently from the housing 1 so as to incise the dermis layer of a patient's chest, as will be described below. As illustrated in FIG. 4, an elongate object, indicated at A (as will be described below, in the apparatus 100, this elongate object is in fact the trocar 3), may pass between the cutting portions 104a, 104b while moving in a distal direction, thus separating them, and bringing the scalpel mechanism 2 into an open position of the scalpel mechanism.

Figure 5:
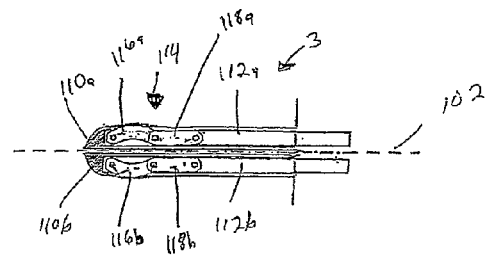
FIGS. 5, 6, and 7 are schematic views of a trocar of the apparatus shown in FIG. 1, at different stages of its operation.
Figure 6:
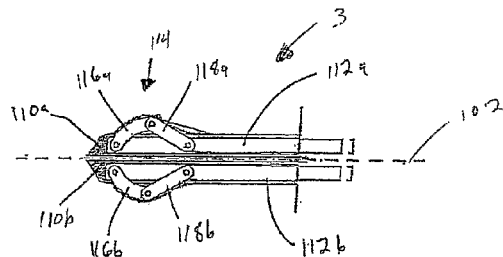
Figure 7:
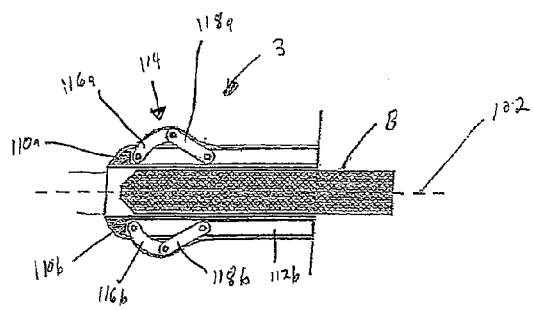

As illustrated in FIGS. 5 through 7, the trocar 3 comprises pointed distal end portions 110a, 110b, first and second trocar portions 112a, 112b, and a trocar head, generally indicated at 114, adjacent the distal end portions. The trocar head 114 comprises distal and proximal arm portions 116a, 116b, 118a, 118b. The distal arm portion 116a, 116b are each hingedly articulated, at respective distal ends thereof, to the end portions 110a, 110b of the trocar, and are each hingedly articulated, at respective proximal ends thereof, to their respective associated proximal arm portions 118a, 118b. The proximal arm portions 118a, 118b, are each hingedly articulated, at respective distal ends thereof, to the end proximal ends of their respective associated distal arm portions 116a, 116b, and are each hingedly articulated, at respective proximal ends thereof, to the main trocar portion 112.

The trocar head 114 is provided with expansion means, such as torsion springs (not illustrated) to spontaneously bring or urge it into an expanded position, as illustrated in FIG. 6, wherein the hinge portions between the distal and proximal end portions are separated from one another, i.e., the trocar head protrudes radially from the trocar 3. In the presence of an inwardly-directed radial force, the trocar head 114 is retained in a compressed position, for example as illustrated in FIG. 5, wherein it is substantially flush with the trocar, i.e., it does not protrude radially therefrom.

The trocar 3 is further provided with a stopping mechanism (not illustrated) which may be activated by trocar portions 112a, 112b when the trocar head assumes its expanded position. The stopping mechanism may be any suitable arrangement which fixes the position of the trocar 3 relative to the housing. It may be activated, e.g., by the sudden distal movement of the main trocar portion 112 due to the rapid expansion of the trocar head 114.

As illustrated in FIG. 7, the trocar 3 may be brought into an open position by separating the trocar portions 112a, 112b from one another, so as to allow passage therethrough of an elongate object, illustrated at B (as will be described below, in the apparatus 100, this elongate object is in fact the drainage tube 4).

As illustrated in FIG. 8, the drainage tube 4 is formed as a substantially hollow, elongate member with a longitudinal passage 120 traversing axially therethrough. It comprises, at its distal end, an expandable balloon portion, generally indicated at 122. The balloon portion 122 comprises a main entrance aperture 124, which brings the longitudinal passage 120 into fluid communication with the area outside and distally adjacent the drainage tube 4, and radial inflatable chamber 126. The chamber is formed with venting apertures 128, which brings the longitudinal passage 120 into fluid communication with the area outside and radially adjacent the balloon portion 122 of the drainage tube 4. The entrance aperture 124 and venting apertures 128 permit the drainage of trapped air from the patient. In addition, the drainage tube 4 comprises an indicator unit, which is generally indicated at 130 and whose operation will be described below, and a proximal portion, generally indicated at 132. The proximal portion 132 comprises a proximal aperture 134, and a plurality of radial apertures 136. Air which is drained from the patient via the main entrance aperture 124 and the venting apertures 128 exit the apparatus 100 via the proximal aperture 134 and the radial apertures 136. A one-way valve 138 is disposed in the longitudinal passage 120 within or near the proximal portion 132.

As illustrated in FIG. 9, the drainage tube 4 is further provided with an indicator channel 140 and inflation channel 142 formed along its length. The indicator channel 140 is in fluid communication at a proximal end thereof to the interior distal portion of the indicator unit 130, and at a distal end thereof to a distal end of the longitudinal passage 120. The significance of this will be clarified when the operation of the indicator unit 130 is described. The inflation channel 142 traverses substantially the entire length of the drainage tube, bringing the distal and proximal ends thereof into fluid communication with one another.

Figure 11:
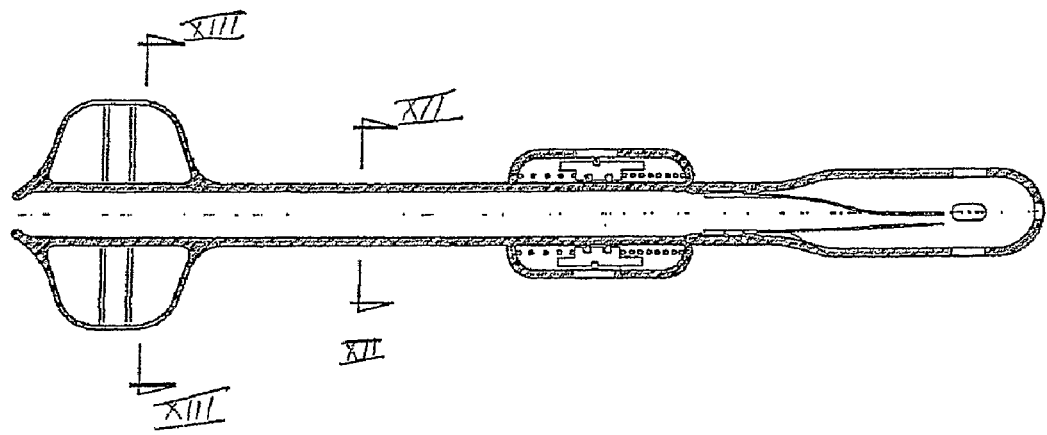
FIG. 11 is a longitudinal cross-sectional view of the tube shown in FIG. 8, with the balloon at its distal end inflated.
Figure 12:
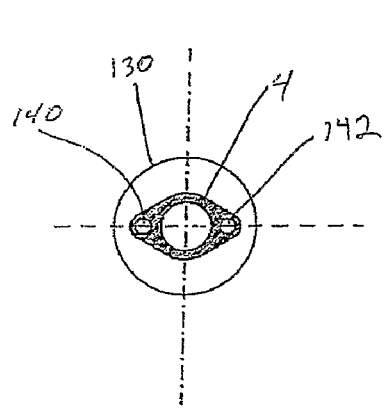
FIGS. 12 and 13 are cross-sectional views of the tube shown in FIG. 8, taken along lines XII-XII and XIII-XIII, respectively.
Figure 13:
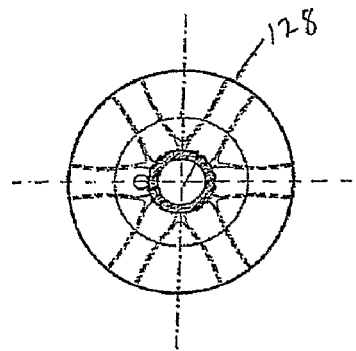
Figure 14:
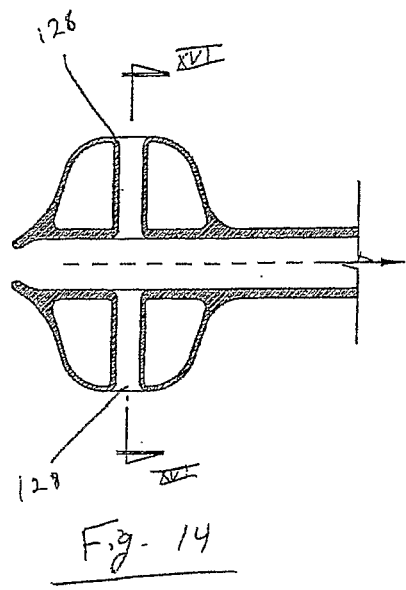
FIGS. 14 and 15 are longitudinal cross-sectional views of a tube with an inflated balloon, similar to that shown in FIG. 11, with the balloon having different alternative designs.
Figure 16:
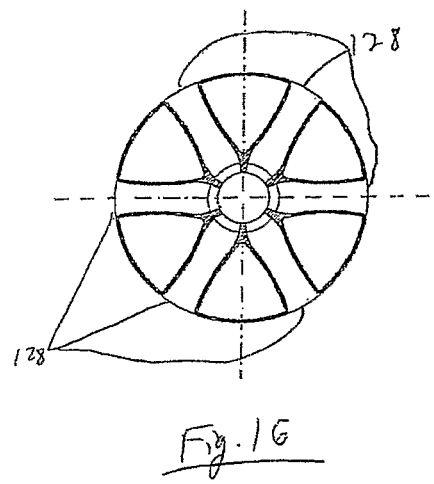
FIGS. 16 and 17 are cross-sectional views of the tubes shown in corresponding FIGS. 14 and 15, taken along respective lines XVI-XVI and XVII-XVII.
Figure 15:
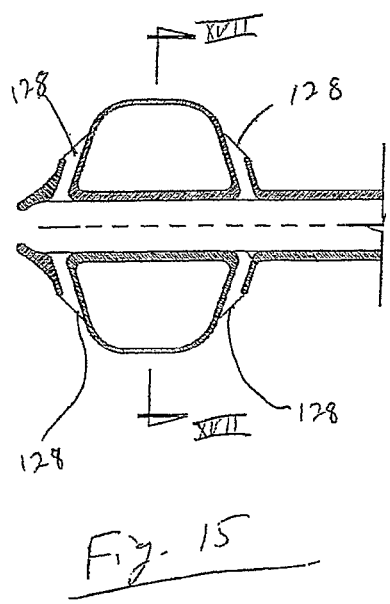
Figure 17:
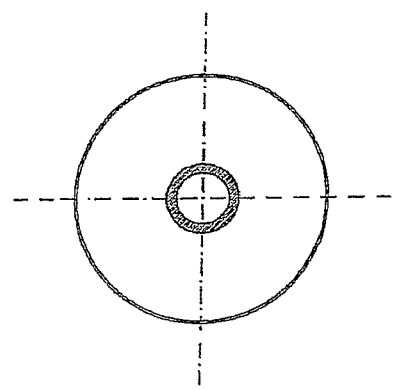

FIGS. 11 through 13 illustrated the same views of the drainage tube 4 as illustrated in FIGS. 8 through 10, respectively, except with the balloon portion 122 in an inflated position. In this position, the venting apertures 128 are better seen in cross-section, as illustrated in FIG. 13. Alternative configurations of the venting apertures are illustrated in FIGS. 14 through 17.

FIGS. 18 through 20 illustrate the operation of the indicator unit 130. As noted above, the indicator channel is in fluid communication with both the interior distal portion of the indicator unit 130, and with the distal end of the longitudinal passage 120. In addition, the proximal end of the indicator unit 130 comprises a vent 150 which is adapted to be open to the atmosphere, at least when the drainage tube has been introduced into the patient's chest cavity.

In addition, the indicator unit 130 comprises an indicator slide 152, which is adapted to move axially along the length of the drainage tube 4 within the indicator unit 130. The indicator slide 152 is provided with indicia, such as color-coding, words, illustrations, etc., a first indicium on the exterior surface of a proximal portion 152a of the indicator slide, and a second indicium on the exterior surface of a distal portion 152b of the indicator slide. The first indicium is indicative that the longitudinal passage 120 is not blocked, and the second indicium is indicative that the longitudinal passage is blocked or obstructed in some way.

Furthermore, the indicator unit 130 comprises radial openings 154 through which the indicia may be viewed, and is provided with distal and proximal biasing members, 156a and 156b. The biasing members, which may be coils springs as illustrated in FIGS. 18 and 19, are designed so that absent any net exterior force on the indicator slide 152, the slide remains in a neutral position, wherein the proximal portion 152a, and thus the first indicium, is visible through the radial opening 154.

As illustrated in FIG. 18, in the event that air can flow freely along the entire length of the longitudinal passage 120 (i.e., the drainage tube 4 is venting the chest cavity of the patient properly), which is the case when there is no obstruction therein, the pressure of the air at the distal end of the longitudinal passage is equal to ambient air pressure. Thus, there is no net external force acting on the indicator slide 152, which remains in its neutral position, and the first indicium is visible through the radial opening 154.

As illustrated in FIG. 19, in the event that air flow through the longitudinal passage 120 is obstructed (i.e., the drainage tube is not properly venting the chest cavity of the patient), the pressure of the air at the distal end of the longitudinal passage exceeds the ambient air pressure. Thus, there is a net external force acting on the indicator slide 152 in the proximal direction, which exceeds the force exerted on the indicator slide by the proximal biasing member 156b. The indicator slide 152 thus moves axially along the drainage tube 4 within the indicator unit 130, bringing the second indicium into a position where it is visible through the radial opening 154. A user can then quickly ascertain if the drainage tube is venting properly. When the obstruction is cleared, the indicator slide 152 is return to the neutral position by the force of the proximal biasing member 156b acting thereon in a distal direction, and the first indicium is again visible through the radial opening 154.

In addition, the indicating unit 130 may be provided with a device (not illustrated) which emits an audible alert in the case of an obstruction, which may be triggered when the indicator slide 152 is moved proximally within the indicator unit 130.

Figures 21, 22:
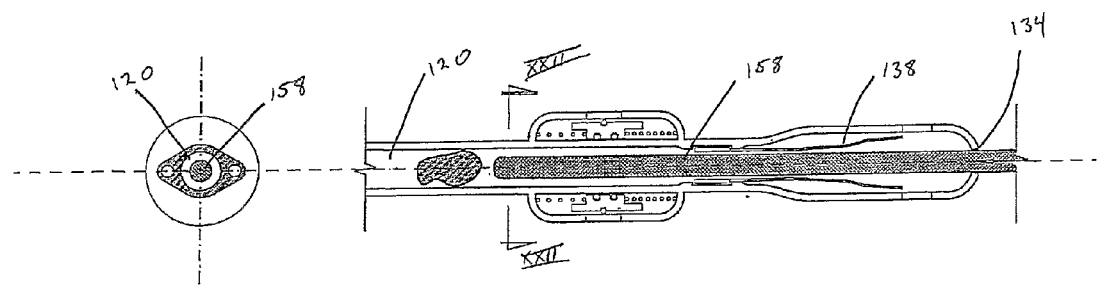
FIG. 21 is longitudinal cross-sectional view of a portion of the tube shown in FIG. 8 including a pressure indicator and a proximal end of the apparatus, with an obstruction removal rod inserted therein.
FIG. 22 is a cross-sectional view of the portion of the tube shown in FIG. 21, taken along a line XXII-XXII.

FIGS. 21 and 22 illustrate how a rod 158 may be used to clear an obstruction within the longitudinal passage 120 of the drainage tube 4. The rod 158 is allowed passage into the longitudinal passage 120 via the one-way valve 138.

Figure 23A:
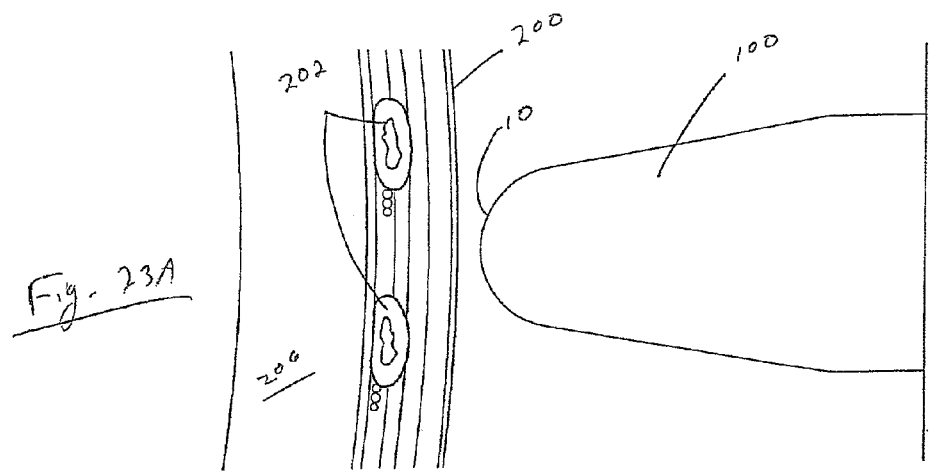
FIGS. 23A through 23L schematically show different stages of insertion of an apparatus according to the present invention into a patient's chest.
Figure 23B:
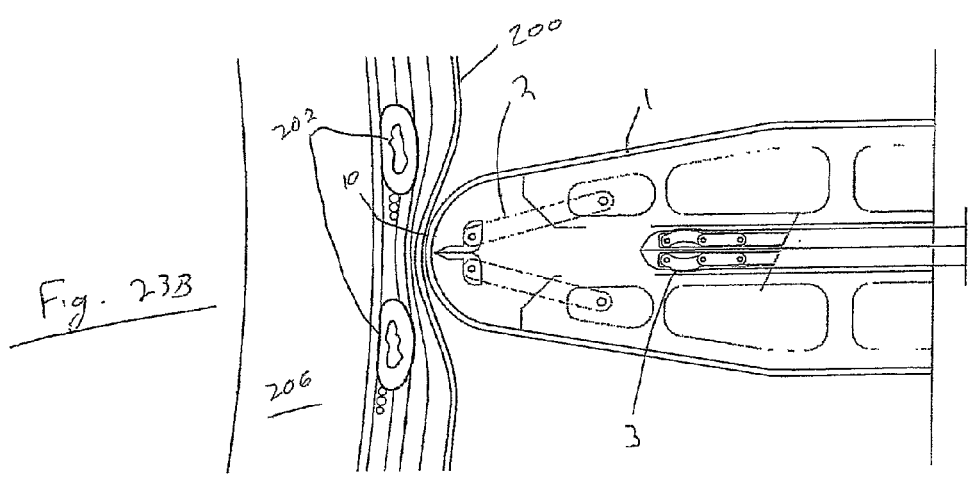

An example of operation of the apparatus 100 is illustrated in FIGS. 23A through 23L. As seen in FIG. 23A, the apparatus 100 approaches a patient's chest 200. The distal end 10 thereof enables the apparatus to "locate" the area between adjacent ribs 202, i.e., to be easily and automatically brought to a position where it rests between two adjacent ribs when pressed against the chest area of a patient, as illustrated in FIG. 23B. In addition, FIG. 23B illustrates the scalpel mechanism 2 in its closed position, and the trocar 3 in its closed position with the trocar head 114 in its compressed position. It will be noted that the interior of the housing may be formed so as to retain the trocar head 114 in the compressed position, at least in its initial position.

Figure 23C:
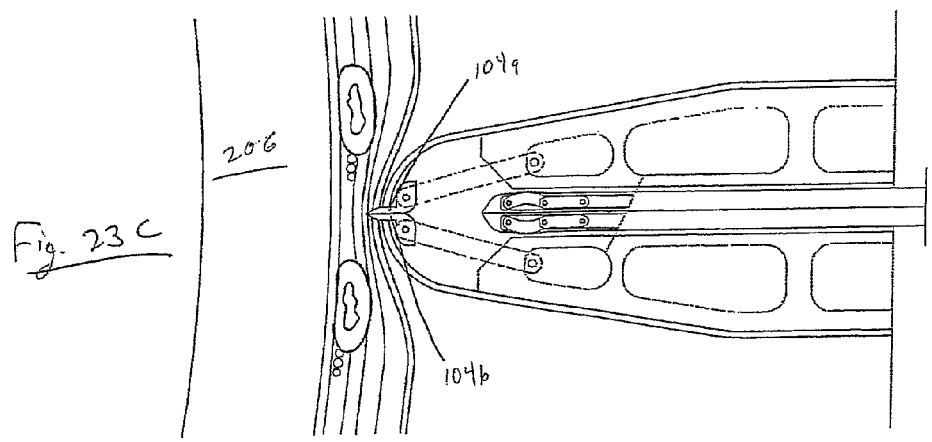

As illustrated in FIG. 23C, the scalpel portion 2 is moved distally within the housing 1, until is pierces the distal end 10 thereof, thus assuming its protruding position. With the protrusion of the cutting portions 104a, 104b from the housing, the dermis layer 204 of the patient's chest 200.

Figure 23D:
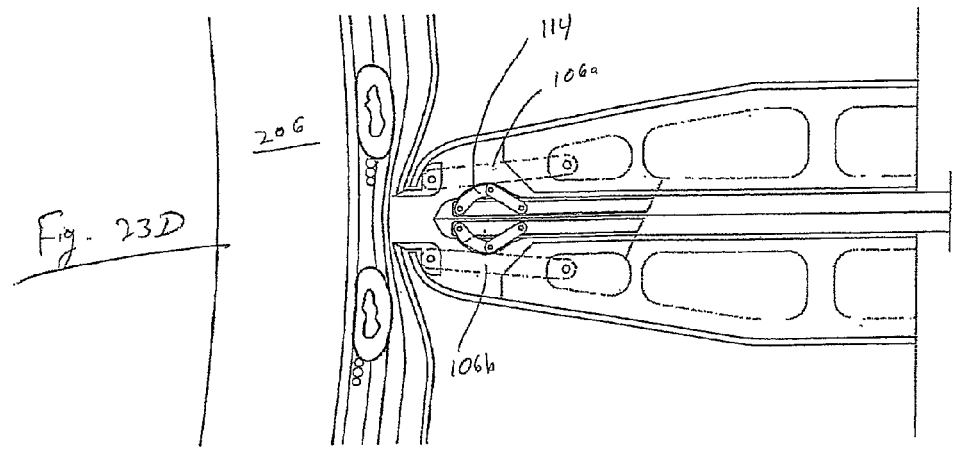

As illustrated in FIG. 23D, the trocar 3 begins to advance distally within the housing 1, toward a position wherein the trocar head 114 is no longer retained in its collapsed position. Thus, it assumes its expanded position. In this position, the trocar head 114 engages the scalpel supports 106a, 106b, separating the distal ends thereof, and bringing the scalpel mechanism 2 into its open position. This opens the dermis of the patient.

Figure 23E:
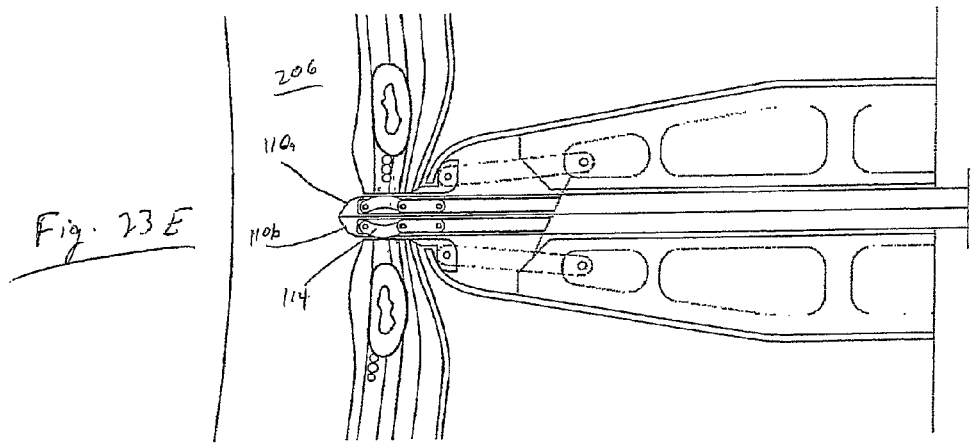

As illustrated in FIG. 23E, the trocar 3 further advances distally, until the trocar head 114 passes the cutting portions 104a, 104b of the scalpel mechanism 2. The pointed distal end portions 110a, 110b of the trocar pierce the remainder of the chest wall of the patient, until reaching the chest cavity 206. When passing the cutting portions 104a, 104b, the resistance of the patient's chest exerts an external, radially-inwardly directed force on the trocar 3, which brings the trocar head 114 into its compressed position.

Figure 23F:
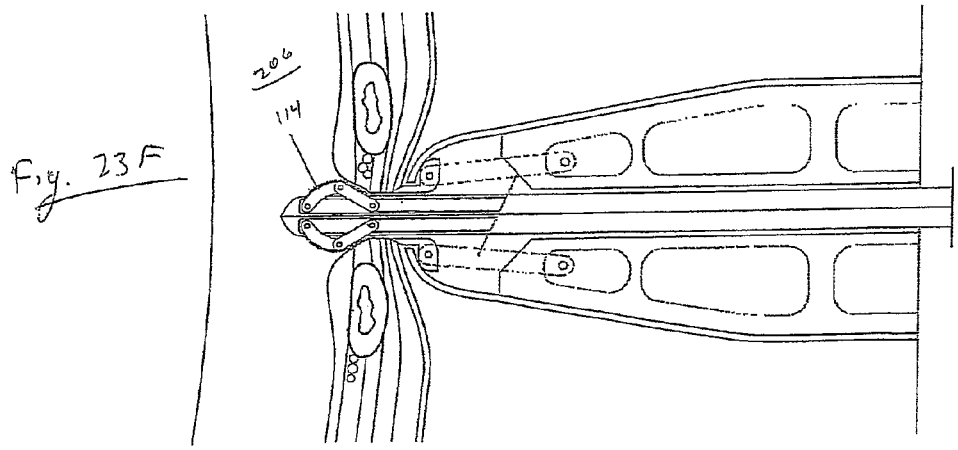

As illustrated in FIG. 23F, when the trocar head 114 passes the chest wall and reaches the chest cavity 206, it spontaneously brings itself into its expanded position, under the influence of the means provided to urge it into the expanded position. As described above, this causes the stopping mechanism of the trocar 3 to be activated, preventing the trocar from being inserted any further than is necessary and from causing damage to internal organs of the patient.

Figure 23G:
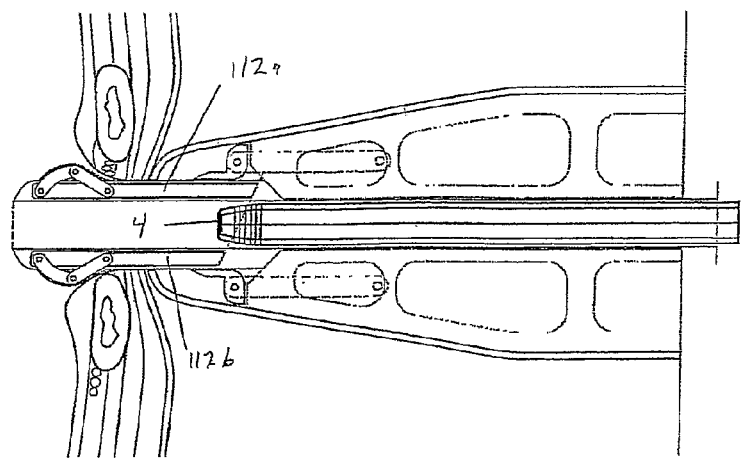
Figure 23H:
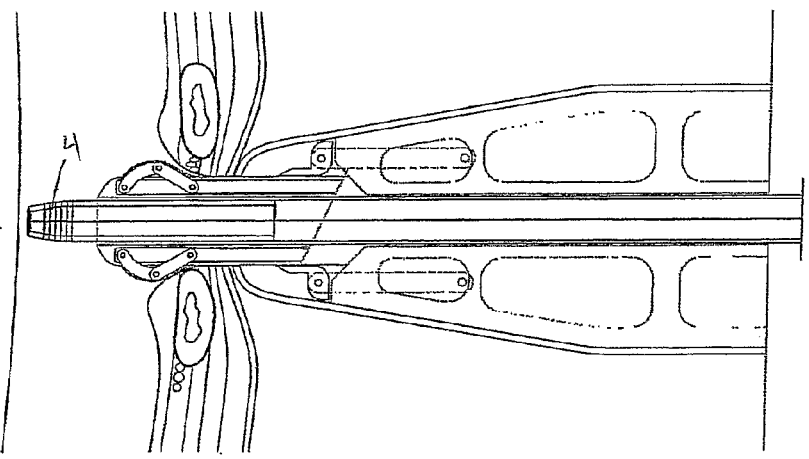

As illustrated in FIGS. 23G and 23H, the drainage tube 4 advances distally within the housing, such that it brings the trocar 3 into its open position. The distal end thereof can then easily enter the chest cavity 206.

Figure 23I:
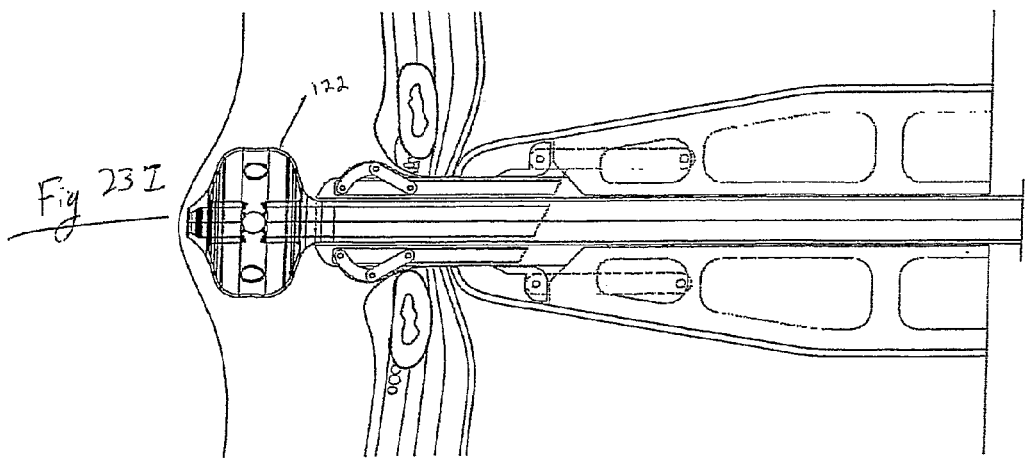

As illustrated in FIG. 23I, once the distal end of the drainage tube 4 has entered the chest cavity 206 and the balloon portion 122 thereof has cleared the distal end of the trocar 3, the balloon portion is inflated, for example by the user blowing or pumping fluid or air thereto via the inflation channel 142.

Figure 23J:
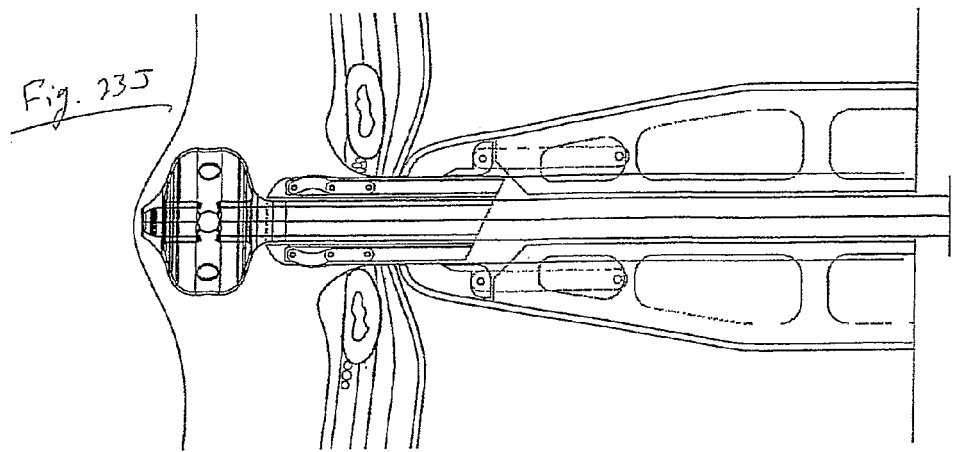
Figure 23K:
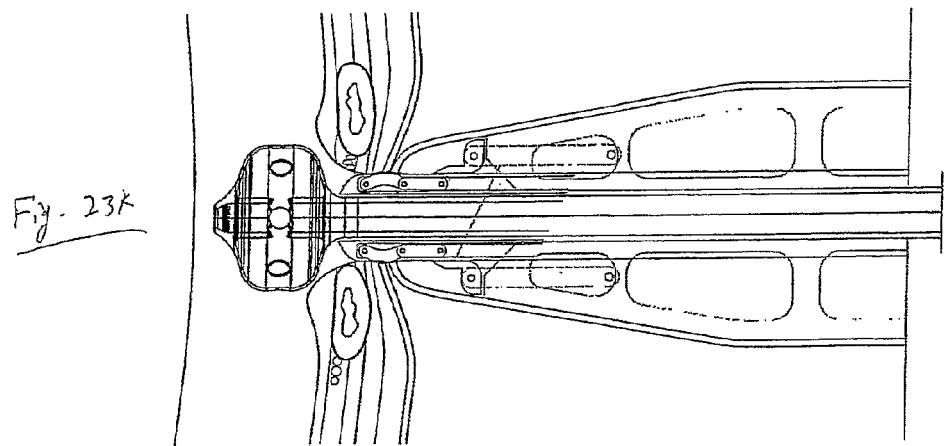
Figure 23L:
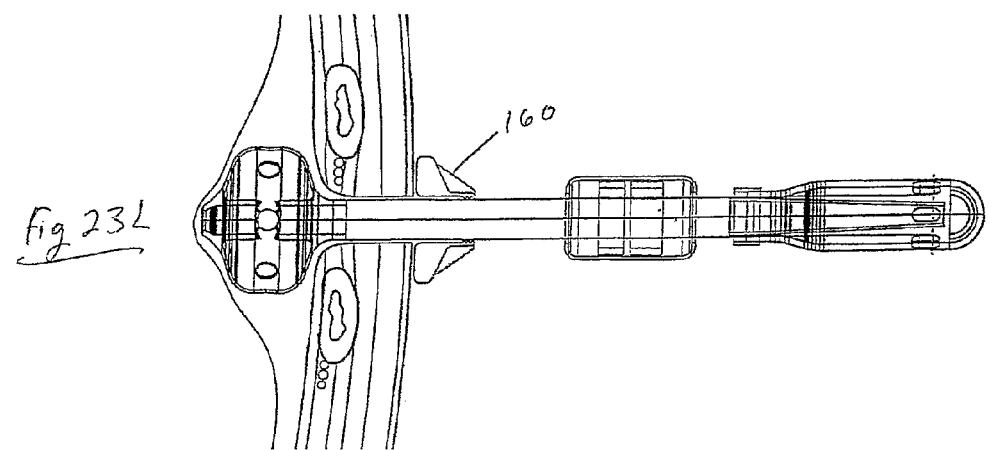

At this point, as illustrated in FIGS. 23J through 23L, the apparatus 100 is removed. During the removal, the trocar 3 is pulled distally, stretching the trocar head 114 and thus bringing it into its collapsed position. Thus, it can be easily removed, leaving the drainage tube 4, with its inflated balloon portion 122, within the chest cavity 206 of the patient. It will be appreciated that the inflated balloon portion 122 helps anchor the drainage tube 4 in place. A stopper 160 may be provided around the drainage tube 4 adjacent the chest 200 of the patient in order to further secure the drainage tube in its position and from sliding in to the chest cavity 206.

Once the drainage tube 4 has been inserted as above, the chest cavity 206 may be vented via the longitudinal passage 120 thereof, by entering via the main entrance aperture 124 and/or the venting apertures 128, end exiting via the proximal aperture 134 and/or the radial apertures of the proximal portion 132.

Figure 24:
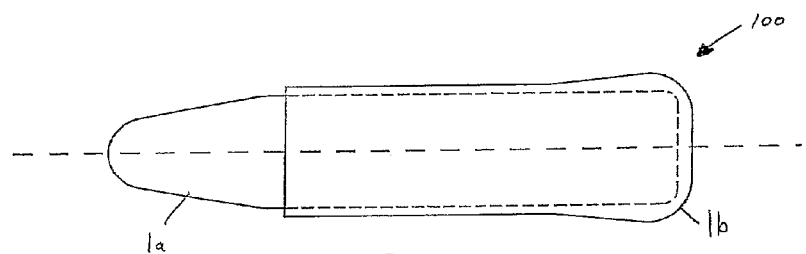
FIGS. 24 and 25 are schematic exterior views of the apparatus shown in FIGS. 23A to 23L in respective closed and open positions, according to one modification.
Figure 25:
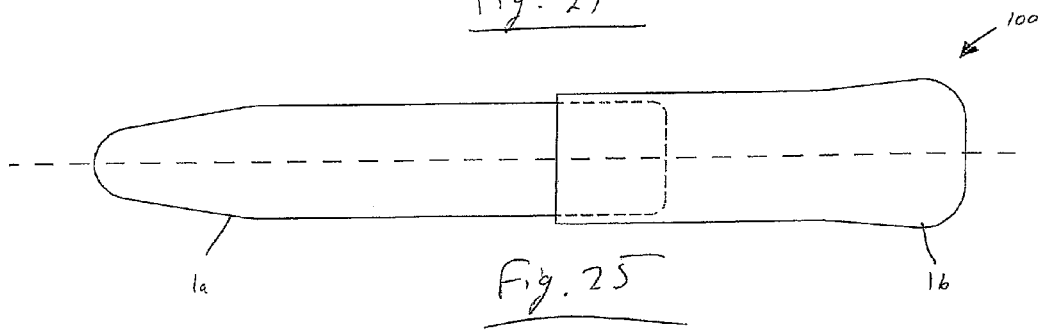

According to one modification, the apparatus 100 may be constructed such that the housing is formed comprising distal and proximal telescoping portions 1a, 1b, as illustrated in FIGS. 24 and 25. This construction permits, inter alia, the apparatus 100 to be provided in a compact state. In addition, it allows the apparatus 100 to be provided such that it is initially in an unarmed state, i.e., not immediately available for insertion into a patient's chest cavity as described in reference to FIGS. 23A through 23L, with the user arming it prior to use, as will be further explained below. An activation mechanism (not illustrated), such as a spring (or system of springs), a hydraulic system, or any other suitable mechanism which is adapted to store potential energy and quickly convert it to kinetic energy, may be provided within the housing. The activation mechanism is designed such that is acts upon the scalpel mechanism, trocar, and drainage tube in sequence so as to carry out the operation described in reference to FIGS. 23A through 23L.

According to this modification, the activation mechanism is initially in a rest state, with the distal telescoping portion 1a received to its maximum extent within the proximal telescoping portion 1b. In this position, the activation mechanism does not store the potential energy necessary to act as above. Immediately prior to use, the user pulls the distal and proximal telescoping portions 1a, 1b apart from one another, into the position illustrated in FIG. 25. This provides potential energy to the activation mechanism, and positions it to act upon the scalpel mechanism, trocar, and drainage tube in the proper sequence as mentioned above. In addition, the apparatus 100 may comprise a mechanism, such as a catch, adapted to keep the distal and proximal telescoping portions 1a, 1b in this position until manually released.

Once the apparatus is placed on the patient's chest, for example as described in reference to FIGS. 23A and 23B, the user releases the mechanism which was keeping the distal and proximal telescoping portions 1a, 1b in the position illustrated in FIG. 25, which causes operation of the apparatus as described in reference to FIGS. 23C through 23L.

Those skilled in the art to which this invention pertains will readily appreciate that numerous changes, variations and modifications can be made without departing from the scope of the invention mutatis mutandis.

The invention claimed is:

1. An apparatus for the introduction of a drainage tube into a patient's chest cavity, the apparatus comprising:
   a housing having a distal end, a proximal end, and a longitudinal axis;
   a scalpel mechanism comprising two cutting portions at a distal end thereof and being mounted inside the housing, said scalpel mechanism being adapted to penetrate said distal end of the housing toward a protruding position therefrom, and being operable in said protruding position between a closed position in which the cutting portions are adjacent one another and adapted to make an incision in the dermis of the patient, and an open position in which the cutting portions are spaced from one another forming a scalpel passage along said longitudinal axis between the cutting portions; and
   a trocar with a proximal end and a distal end and comprising first and second trocar portions being mounted inside the housing, each extending along the length of the trocar and being separable from one another; said trocar being operable between an closed position wherein said first and second trocar portions are substantially adjacent one another, and an open position in which said first and second trocar portions are spaced from one another and adapted for the introduction of the drainage tube therethrough.

2. An apparatus according to claim 1, wherein the distal end of the housing is formed as a rounded tip.

3. An apparatus according to claim 1, further comprising means for securing the drainage tube within the chest cavity when inserted therein.

4. An apparatus according to claim 3, wherein, when the drainage tube is secured within the chest cavity, at least the housing, scalpel mechanism, and trocar are adapted to be removed therefrom.

5. An apparatus according to claim 1, wherein said trocar comprises at its proximal end a stopping mechanism adapted to prevent the trocar from progressing distally within the chest cavity beyond a predetermined amount.

6. An apparatus according to claim 5, said trocar comprising a trocar head being operable in a compressed position and an expanded position in which it protrudes radially from the rest of the trocar, and comprising expansion means adapted to spontaneously bring the trocar head into its expanded position, said stopping mechanism being adapted to be activated upon expansion of the trocar head.

7. An apparatus according to claim 1, wherein said trocar further comprises a trocar head adjacent the distal end of the trocar, said trocar head being operable in a compressed position in which it is substantially flush with the rest of the trocar, and an expanded position, in which it protrudes radially therefrom.

8. An apparatus according to claim 7, said trocar head comprising expansion means adapted to spontaneously bring the trocar head into its expanded position.

9. An apparatus according to claim 7, wherein said trocar head is adapted to remain in its expanded position in the absence of any net external force thereto, and to assume its compressed position in the presence of an inwardly directed radial force.

10. An apparatus according to claim 9, said trocar head comprising adjacent or at its distal end two or more hinged arms, each comprising two arm segments hingedly articulated to its adjacent segment or the trocar, each arranged such in the compressed and expanded positions of the trocar head, distal and proximal ends thereof remain equal distances from the longitudinal axis.

11. An apparatus according to claim 1, wherein said housing is adapted to enclose said trocar so as to retain the trocar in its closed position with the trocar head in its compressed position.

12. An apparatus according to claim 1, said apparatus constituting a part of a device for chest drainage with said tube constituting a part of said device and being mounted in said housing before the introduction of the drainage tube into the patient's chest cavity.

13. An apparatus according to claim 12, said tube comprising a proximal end and a distal end and being adapted to pass through said trocar passage until its distal end protrudes therefrom along said longitudinal axis, to a predetermined extent necessary for the insertion into the chest.

14. An apparatus according to claim 13, wherein the tube is fitted at its distal end with an inflatable balloon portion to secure it within the chest cavity when inserted therein.

15. An apparatus according to claim 14, wherein said balloon portion is formed with drainage channels which provide fluid communication between the exterior of the balloon portion with the interior of the tube.

16. An apparatus according to claim 13, wherein said tube comprises a one-way valve at its proximal end.

17. An apparatus according to claim 13, wherein said tube is fitted with a stopper adapted to prevent movement thereof in the distal direction when the housing when said scalpel mechanism and said trocar are removed from the tube.

18. An apparatus according to claim 13, wherein said tube is fitted with an indicating unit, including a pressure indicator and a channel extending from the distal end of the tube, and open to the exterior thereof, to the pressure indicator.

19. A method of insertion of a drainage tube into a patient's chest cavity, including:
    providing an apparatus according to claim 1;
    pressing the distal end of the base against the patient's chest, until the drainage tube is within the chest cavity;
    inflating a balloon portion, provided at a distal end of the drainage tube; and
    removing the apparatus from the patient, leaving the drainage tube.

20. A method according to claim 19, further including the step of providing a stopper on the drainage tube adjacent the patient's chest.

* * * * *